(12) United States Patent
Pospisil et al.

(10) Patent No.: US 7,686,613 B2
(45) Date of Patent: Mar. 30, 2010

(54) NARROW CERAMIC SELF-LIGATING ORTHODONTIC BRACKET

(75) Inventors: Jirina V. Pospisil, Hacienda Heights, CA (US); Glenys A. Thorstenson, Azusa, CA (US); Joyce C. Ho, Temple City, CA (US); Joan V. Brennan, Sierra Madre, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/775,253

(22) Filed: Jul. 10, 2007

(65) Prior Publication Data

US 2009/0017411 A1  Jan. 15, 2009

(51) Int. Cl.
*A61C 3/00*  (2006.01)
(52) U.S. Cl. ...................................... 433/11
(58) Field of Classification Search ............... 433/10, 433/11
See application file for complete search history.

(56) References Cited

U.S. PATENT DOCUMENTS

| | | | |
|---|---|---|---|
| 4,068,379 A * | 1/1978 | Miller et al. ............ 433/9 |
| 4,954,080 A | 9/1990 | Kelly et al. |
| 5,358,402 A | 10/1994 | Reed et al. |
| 5,366,372 A | 11/1994 | Hansen et al. |
| 5,380,196 A | 1/1995 | Kelly et al. |
| 5,439,379 A | 8/1995 | Hansen |
| 5,906,486 A | 5/1999 | Hanson |
| 6,071,119 A | 6/2000 | Christoff et al. |
| 6,193,508 B1 | 2/2001 | Georgakis |
| 6,302,688 B1 | 10/2001 | Jordan et al. |
| 6,325,622 B1 | 12/2001 | Kelly et al. |
| 6,554,612 B2 * | 4/2003 | Georgakis et al. ....... 433/11 |
| 6,582,226 B2 | 6/2003 | Jordan et al. |
| 6,648,638 B2 | 11/2003 | Castro et al. |
| 6,984,127 B2 | 1/2006 | Lai |
| 7,014,460 B2 | 3/2006 | Lai et al. |
| 7,104,791 B2 | 9/2006 | Hanson |
| 7,140,875 B2 | 11/2006 | Lai et al. |
| 7,140,876 B2 | 11/2006 | Cinader et al. |
| 7,192,274 B2 | 3/2007 | Stadtmiller et al. |
| 2002/0197581 A1 | 12/2002 | Georgakis et al. |
| 2004/0086825 A1 | 5/2004 | Lai et al. |

(Continued)

OTHER PUBLICATIONS

Pending U.S. Appl. No. 11/536,724, filed Sep. 29, 2006.

*Primary Examiner*—Ralph A Lewis
(74) *Attorney, Agent, or Firm*—Philip P. Soo (57) ABSTRACT

A ceramic orthodontic bracket has a centrally located clip for retaining an archwire in an archwire slot. The body of the bracket includes a mesial section, a distal section, and a bridge section, wherein the bridge section extends through, and retains, the clip. The bridge section also includes a recess adjacent to the bridge section that facilitates debonding of the bracket from a patient's tooth. Preferably there are gaps on one or both sides of the clip to allow space for debonding of the bracket by applying a mesial-distal compressive force on the bracket and fracturing the bracket along the recess. This configuration allows the overall mesial-distal width of the bracket to be reduced, thereby facilitating the bonding of brackets to narrow and/or maloccluded teeth. Another embodiment includes a stop member that is connected to the base of the bracket and retains the clip on the bridge section.

12 Claims, 3 Drawing Sheets

U.S. PATENT DOCUMENTS

| | | |
|---|---|---|
| 2005/0095549 A1 | 5/2005 | Cinader et al. |
| 2005/0123875 A1 | 6/2005 | Stadtmiller et al. |
| 2006/0024635 A1 | 2/2006 | Lai |
| 2006/0127835 A1 | 6/2006 | Soo et al. |
| 2006/0172249 A1 | 8/2006 | Lai et al. |
| 2008/0138757 A1* | 6/2008 | Lai et al. ............ 433/10 |

* cited by examiner

NARROW CERAMIC SELF-LIGATING ORTHODONTIC BRACKET

BACKGROUND OF THE INVENTION

1. Field of the Invention

The present invention broadly pertains to an appliance used in orthodontic treatment. More particularly, this invention pertains to a ceramic orthodontic appliance that includes a clip for releasably retaining an archwire in an archwire slot of the appliance.

2. Description of the Related Art

Orthodontic therapy is a specialized type of treatment within the field of dentistry associated with the supervision, guidance and correction of malpositioned teeth into proper locations. Orthodontic treatment can be useful in correcting defects in a patient's bite (also called occlusion) along with promoting better hygiene and improving the overall aesthetics of the teeth.

Orthodontic treatment often involves the use of tiny slotted appliances known as brackets, which are generally affixed to the patient's anterior, cuspid, and bicuspid teeth. After the brackets have been placed on the teeth, an archwire is received into the slot of each bracket and acts as a track to guide the movement of respective teeth to orthodontically correct positions. End sections of the archwire are typically captured in appliances known as buccal tubes that are affixed to the patient's molar teeth. After installation in the patient's mouth, the brackets, archwires, and buccal tubes are typically referred to collectively as "braces".

Conventional brackets use an elastomeric ligature or metal ligature wire to secure the archwire in the slot of each bracket. However, there are also appliances known as "self-ligating" brackets, which do not require the use of ligatures. Instead of using a ligature, a self-ligating bracket uses a latch for securing the archwire in place. These types of brackets can be advantageous because levels of sliding resistance between the archwire and the bracket can be reduced, resulting in faster leveling and aligning of teeth. Moreover, the elimination of ligatures can simplify installation and removal of archwires during treatment, improve patient hygiene, and avoid the inconvenience of replacing elastomeric ligatures as a result of ligature staining.

Latches used in self-ligating brackets come in many shapes and sizes, and may comprise a clip, spring member, cover, shutter, bail, or other structure that is coupled to the bracket body and capable of releasably retaining an archwire in the archwire slot. As an example, a bracket used in the SMARTCLIP brand Self-Ligating Appliance System sold by 3M Unitek (Monrovia, Calif.) uses a latch based on two "C"-shaped clips comprising a shape-memory alloy that are coupled to the bracket body. The clips flex open and closed to receive and retain an archwire in response to a clinician applying suitable forces on the archwire. Examples of latches are also described in U.S. Pat. Nos. 6,302,688, 6,325,622, 6,582, 226, 6,984,127, as well as in published U.S. patent application No. 2006/0172249. Aesthetic self-ligating bracket systems made from ceramics or other translucent materials are also possible.

In much the same way that a ligature secures the archwire on both the mesial (i.e. facing towards the center of the patient's dental arch) and distal (i.e. facing away from the center of the dental arch) sides of the bracket, the two clips of the SMARTCLIP brand self-ligating brackets mentioned above are symmetrically disposed on the respective mesial and distal sides of the archwire slot. This latch configuration, however, poses challenges for ceramic self-ligating brackets, which tend to be slightly larger than their metal counterparts. Specifically, problems may arise when bonding brackets to small teeth such as lower anteriors. Because lower anterior teeth are small, collisions (or interferences) can occur between adjacent brackets during bonding and prevent brackets from being located optimally on the tooth. Even in cases where the teeth are sufficiently large, bracket interferences may still occur if teeth are overlapping or have facial (i.e. towards the patient's cheek or lips) surfaces that are angled toward each other. Because lower anterior teeth are often crooked and induce these interferences, the clinician is frequently unable to successfully bond all the brackets on the first appointment and postpones bonding one or two brackets until such time that sufficient space has been created. This in turn extends treatment time and reduces the efficiency of treatment.

Rather than delaying the bonding of brackets, the clinician may choose instead to avoid interferences by bonding some brackets in locations other than their ideal locations. However, this too is disadvantageous because these same brackets will often need to be debonded and re-positioned later in treatment. Bracket re-positioning is not ideal because it requires an additional time investment by the clinician and another potentially uncomfortable procedure for the patient.

As can be appreciated, there is a need for a ceramic bracket that provides the advantages of a self-ligating bracket while minimizing interferences with adjacent brackets.

SUMMARY OF THE INVENTION

The present invention is directed to a ceramic orthodontic bracket that offers a significant advantage over previously known self-ligating brackets. In one aspect of the invention, the bracket includes a generally "C"-shaped latch for releasably retaining an archwire in the archwire slot. This "C"-shaped latch is located between the mesial and distal sections of the bracket. The central location of the clip is advantageous because it enables the bracket to have a reduced mesial-distal width compared to brackets that use mesial and distal clips. A reduced mesial-distal width, in turn, alleviates potential problems with interference between adjacent brackets during bonding. As an additional advantage, reducing mesial-distal width increases the inter-bracket distance. With greater distance for the archwire to deflect or "flex" between brackets, the clinician is able to install larger archwires into the patient sooner in treatment, again enhancing efficiency. By providing tiewings in addition to the centrally-located latch, this bracket gives the clinician flexibility of using the latch for ligation early in treatment, and then increasing sliding resistance by using an elastic O-ring for ligation later in treatment if desired.

In more detail, the present invention is directed in one embodiment to a ceramic orthodontic bracket comprising a mesial section, a distal section, and a bridge section connecting the mesial and distal sections. An archwire slot furthermore extends across the mesial section and the distal section in a generally mesial-distal direction and is located in the facial direction from the bridge section. Located on the lingual side (i.e. towards the patient's tongue) of the bridge section is an elongated groove, which extends in generally occlusal (i.e. towards the biting surfaces of the teeth) and gingival (i.e. towards the patient's gums) directions to provide a stress concentrator during bracket debonding. The bridge section extends through a generally "C"-shaped latch, which has an opening that faces the facial direction for releasably retaining an archwire in the archwire slot. Optionally, the latch is retained on the bridge section by protrusions that extend towards each other and contact the facial side of the bridge section. In other embodiments, the latch is retained on the bridge section by a stop member that is connected to one or both of the mesial section and the distal section.

Optionally, the spacing between the mesial and distal sections of the bracket may exceed the mesial-distal width of the clip by a certain amount to further assist in debonding. Other optional features include an archwire slot liner, or tabs disposed at the ends of the clip to facilitate connection of the latch to the bridge section.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

Figure 1:
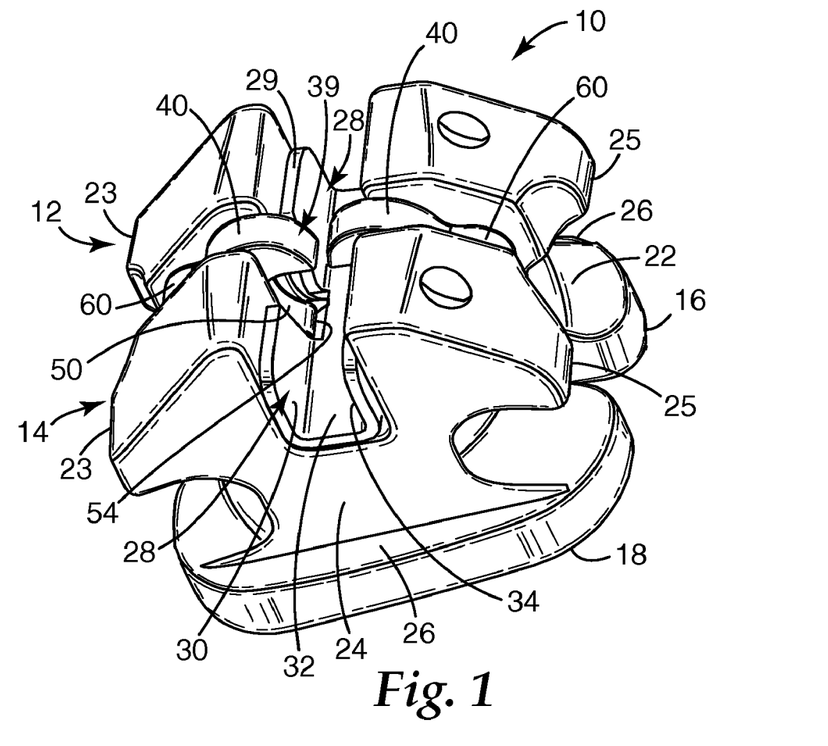
FIG. 1 is a perspective view looking at the distal, gingival and facial sides of a ceramic bracket in accordance with one embodiment of the present invention.
Figure 2:
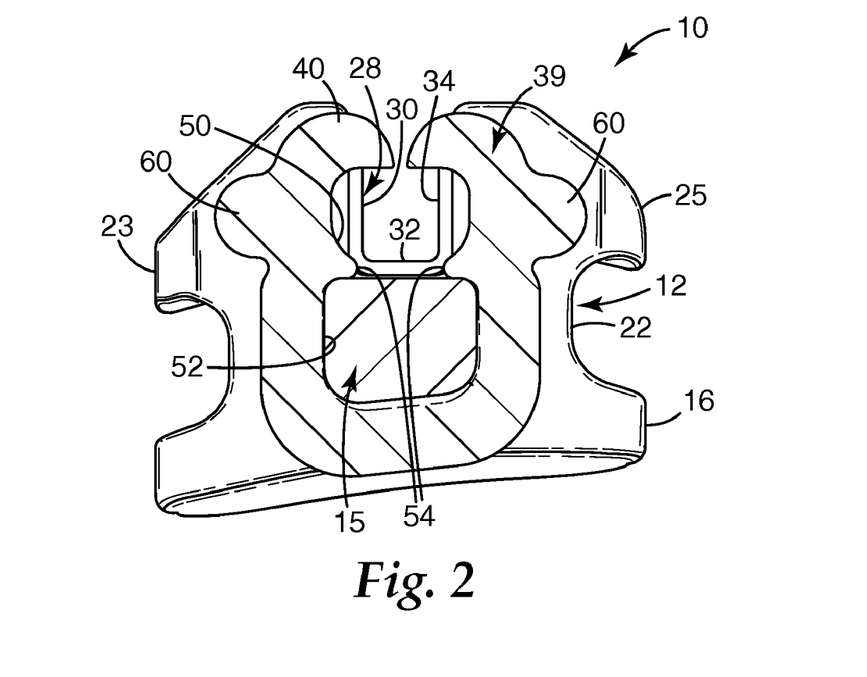
FIG. 2 is a side cross-sectional view of the bracket shown in FIG. 1, showing in greater detail a latch coupled to the bridge section of the bracket.
Figure 3:
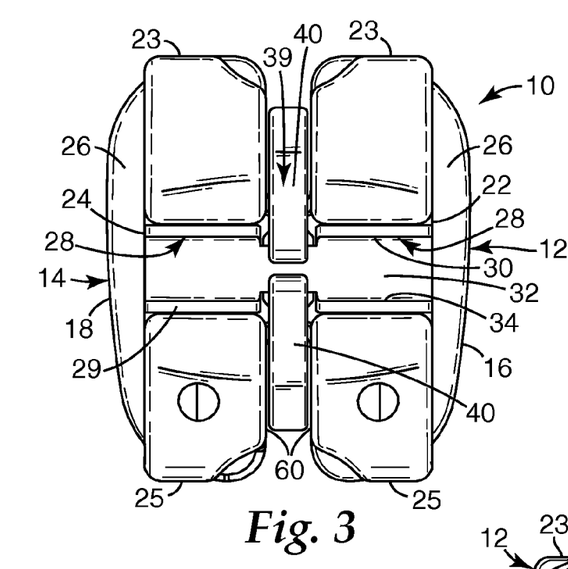
FIG. 3 is a top view looking in the lingual direction of the bracket shown in FIGS. 1 and 2, showing the position of the latch with respect to the mesial section and distal section of the bracket.

An exemplary bracket in accordance with one embodiment of the invention is shown in FIGS. 1-3, and broadly designated by the numeral 10. This particular bracket is adapted to be bonded to the facial surface of a lower anterior tooth of a patient. Alternative embodiments may include brackets designed for bonding to other teeth in the mouth such as cuspids or bicuspids, and molars. Embodiments including buccal tubes or any other type of appliance capable of receiving an archwire for controlling movement of teeth during orthodontic treatment are possible as well.

The bracket 10 includes mesial section 12 and distal section 14, connected to each other by bridge section 15 (visible in the cross-sectional view of FIG. 2). Mesial section 12 and distal section 14 include mesial base 16 and distal base 18, respectively, that are adapted for bonding bracket 10 directly to the tooth of a patient by means of a suitable adhesive. Preferably the bottom surfaces of mesial base 16 and distal base 18 have concave compound contours that match the convex compound contours of the patient's tooth surface. Optionally the bottom surfaces of bases 16, 18 are provided with grooves, particles, recesses, undercuts, a chemical bond enhancement material, or any other material or structure or combination thereof that facilitates bonding the bracket 10 directly to a patient's tooth. Mesial body 22 of mesial section 12 and distal body 24 of distal section 14 extend outwardly in a generally facial direction from respective bases 16, 18. To increase surface area for bonding to the tooth, bracket 10 includes a pair of flanges 26 (shown in FIGS. 1 and 3) that extend past mesial body 22 in the mesial direction from mesial base 16, and past distal body 24 in the distal direction from distal base 18. Flanges 26 could optionally extend laterally in other directions (e.g. gingival or occlusal) although this is not shown.

An archwire slot 28 extends across mesial body 22 and distal body 24 in a generally mesial-distal direction. The archwire slot 28 is located facial to the bridge section 15 and is bounded by three walls: an occlusal wall 30, lingual wall 32, and gingival wall 34, while open in the facial direction. The archwire slot 28 and walls 30, 32, 34 are fixed relative to the sections 12, 14. Although shown flat in the figures, walls 30, 32, 34 could be curved, or part of ridges, bumps, or other types of protrusions. Walls 30, 34 in each body 22, 24 are immovable relative to each other and are parallel to each other. In this embodiment, mesial body 22 and distal body 24 each include an occlusal tiewing 23 and a gingival tiewing 25, although one or more of the tiewings 23, 25 could be omitted if so desired.

Clip 39 is coupled to the bridge section 15 of bracket 10 and located between mesial section 12 and distal section 14. The clip 39 has a generally "C"-shaped configuration and includes a pair of arm portions 40 that extend in the facial directions and then bend inwardly toward each other. Within clip 39 is an archwire-receiving region 50 that is aligned with the archwire slot 28 in sections 12, 14 as well as a bridge-receiving region 52 that is in communication with archwire-receiving region 50. Bridge section 15 extends through the bridge-receiving region 52 of the clip 39. In such fashion, clip 39 is sandwiched between sections 12, 14 and is further held in place by one or more protrusions 54 that contact the facial side of bridge section 15, thereby preventing clip 39 from sliding in the lingual direction. As shown, no other component of bracket 10 is located in the lingual direction of the clip 39.

The clip 39 is shown in its normal, relaxed orientation in FIGS. 1, 2, and 3. However, the arm portions 40 are movable away from each other in order to admit the archwire into the archwire-receiving region 50 when so desired. The smooth, outer edge of the arm portions 40 enables the clip 39 to receive an archwire by pressing the archwire against the outer curved edges of the arm portions 40. As pressure is exerted by the archwire on the curved edges, the arm portions 40 deflect away from each other in order to admit the archwire into the archwire-receiving region 50. As clip 39 is opened, the protrusions 54 slide across the facial side of the bridge section 15. However, the protrusions 54 extend inwardly and toward each other a distance sufficient to remain in contact with the facial side of the bridge section 15 as the clip 39 is opened. As such, the clip 39 remains coupled to the bridge section 15 during such opening movements.

Once the archwire is received in the archwire-receiving region 50, the inherent resiliency of the clip 39 enables arm portions 40 to spring back toward each other and toward their normal, relaxed configuration as shown in FIGS. 1, 2, and 3 in order to retain the archwire in the archwire slot 28. Preferably, but not necessarily, the archwire-receiving region 50 is somewhat larger than the cross-section of the archwire in directions along both an occlusal-gingival reference axis as well as along a facial-lingual reference axis, in order to avoid firm contact between the clip 39 and the archwire. The spaces between the clip 39 and the archwire provide what is often referred to as "passive" ligation. When sufficiently large rectangular archwires are used, however, spaces between the clip 39 and the archwire can be eliminated, leading to "active" ligation. The relative advantages of "passive" and "active" ligation depend on the stage of treatment as well as many other factors, and shall not be examined here.

The clip 39 (which includes the arm sections 40) is sufficiently stiff to retain the archwire in the archwire slot 28 during the course of treatment so long as the forces exerted by the archwire on the bracket 10 are below a certain minimum value in a generally facial direction (more particularly, in a direction opposite to the direction of insertion of the archwire into the archwire slot 28). However, whenever the forces exerted by the archwire on the bracket 10 in the same direction are greater than the minimum value, as might occur when unexpectedly high forces are encountered, the arm portions 40 can move apart from each other to open the clip 39 and release the archwire from the archwire slot 28. Further details regarding such forces are described in the aforementioned U.S. Pat. No. 6,302,688 (Jordan et al.) and U.S. Pat. No. 6,582,226 (Jordan et al.).

The clip 39 preferably releases the archwire from the archwire slot 28 in a generally facial direction whenever the archwire exerts a force in the same direction on the bracket 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 28 during the normal course of orthodontic treatment. As such, the archwire can exert forces on the bracket 10 sufficient to carry out the treatment program and move the associated teeth as desired.

Preferably, the minimum value for self-release (i.e., self-opening) of the latch is substantially less than the force required in the same direction to debond the bracket 10 from the associated tooth. The minimum value for self-release of the latch is preferably less than about one-half of the force required in the same direction to debond the bracket 10 from the associated tooth. For example, if the expected bond strength of the adhesive bond between the bracket 10 and the associated tooth is 16 lbs (7.2 kg) in a facial direction, the latch is constructed to self-release the archwire whenever the archwire exerts a force in the same facial direction on the bracket 10 that is somewhat greater than about 8 lbs (3.6 kg).

To determine the force to release the clip 39, a section of archwire is selected having an area in longitudinally transverse sections that is complemental to (i.e., substantially fills) the cross-sectional area of the archwire slot 28. Next, a sling is constructed and is connected to the archwire section at locations closely adjacent, but not in contact with, the mesial section 12 and distal section 14. Optionally, the sling is welded or brazed to the archwire section. Next, the sling is pulled away from the bracket 10 while the bracket 10 is held in a stationary position, taking care to ensure that the longitudinal axis of the archwire section does not tip relative to the longitudinal axis of the archwire slot 28. The force to release the clip 39 may be determined by the use of an Instron testing apparatus connected to the sling, using a crosshead speed of 0.5 in/min (1.3 cm/min). Alternatively, a cyclic tester (such as Model 300 from APC Dynamics of Carlsbad, Calif.) may be used along with a force transducer (such as Model 208C01 from PCB of Buffalo, N.Y.) to measure the force.

The clip 39 may have additional features that provide an advantage in the assembly of bracket 10. For example, in FIGS. 1 and 2, clip 39 includes a pair of tabs 60 located near the ends of arm portions 40 in a facial direction from the protrusions 54 and extend away from each other in the gingival and occlusal directions. Tabs 60 can assist in providing a purchase point for a manufacturing device to grip and spread apart the arm portions 40 during installation of clip 39 onto the bridge section 15 of the bracket 10. Once the arm portions 40 are spread apart, the clip 39 is moved in a facial direction into the space between the mesial and distal sections 12, 14 until the protrusions 54 are located in a facial direction relative to the bridge section 15. The tabs 60 are then released and the clip 39 springs back to its relaxed configuration as shown in FIG. 2.

Optionally, the clip 39 is cut from a flat section of metallic stock material. Suitable metallic materials include shape memory alloys such as alloys of nitinol and beta-titanium. The clip 39 may be cut from the stock material using a stamping, die cutting, chemical etching, EDM (electrical discharge machining), laser cutting or water jet cutting process. As another option, the clip 39 could be formed and then heat-treated to set its shape. Other suitable clips and possible optional features are given in U.S. Patent Publication Nos. 2006/0024635 (Lai) and 2006/0172249 (Lai et al.).

Should the clinician desire a more "active" ligation or increased sliding resistance, the use of the clip 39 to secure an archwire in archwire slot 28 of bracket 10 may be supplemented by the use of an elastic ligature or metal ligature wire looped and tightened around tiewings 23, 25 and over the facial side of the archwire.

Figure 4:
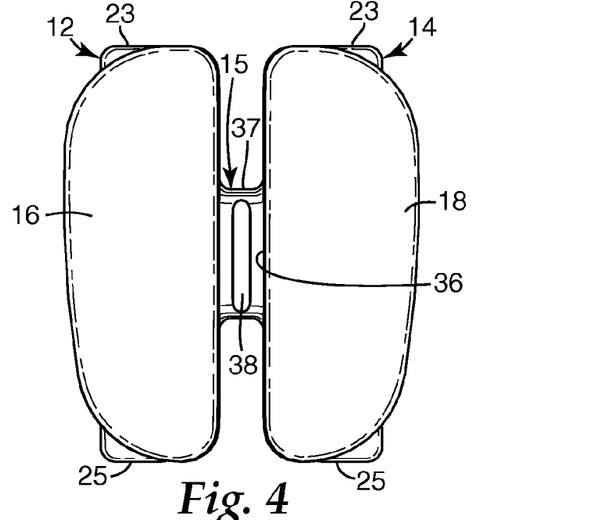
FIG. 4 is a bottom view looking in the facial direction of the bracket shown in FIGS. 1-3 with the latch removed, revealing the elongated groove located on the lingual side of the bridge section of the bracket.
Figure 5:
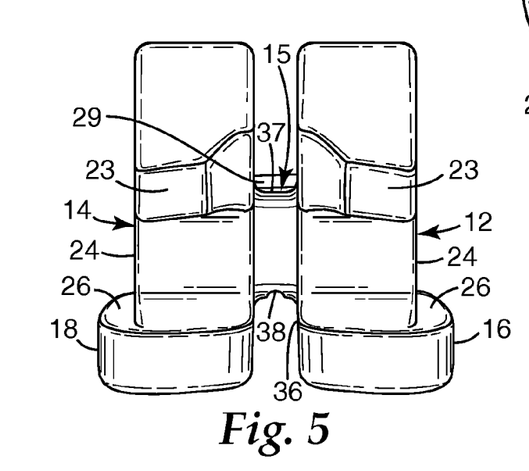
FIG. 5 is a side view looking in the gingival direction of the bracket shown in FIGS. 1-3 with the latch removed, revealing the elongated groove.

FIGS. 4 and 5 show respective bottom and side views of bracket 10 with clip 39 removed from view to reveal additional details around the bridge section 15. A recess 36 is defined by the space located lingual to bridge section 15 and between bases 16, 18. As can be appreciated by FIGS. 1-3, when bracket 10 is fully assembled, a portion of clip 39 extends in the recess 36. Also, bridge section 15 includes an elongated groove 38 that is located on the lingual side of bridge section 15 and extends in a generally occlusal-gingival direction. Elongated groove 38 has a generally U-shaped or V-shaped bottom (or facial-most surface) that is spaced in a facial direction away from the adjacent lingual surfaces of bridge section 15. The elongated groove 38 interrupts the continuity of the lingual surface contour of bridge section 15 and reduces the labial-lingual thickness of the bridge section 15 at its narrowest section. Optionally and as depicted in FIG. 5, the groove 38 has a generally "U"-shaped cross-sectional configuration in reference planes perpendicular to its longitudinal axis.

A line of weakness extends in a generally occlusal-gingival direction along the bridge section 15 and is surrounded by the clip 39. Preferably and as shown, the line of weakness comprises a thin frangible web 37 that bisects the bridge section 15 and integrally connects the mesial and distal sides of bridge section 15. The thin and frangible web 37 has a cross-sectional area that allows bridge section 15 to fracture when sections 12, 14 are urged toward each other in a manner such that one or both of sections 12, 14 pivot in direction(s) toward each other in an arc and about a reference axis that is generally parallel to the occlusal-gingival axis of the elongated groove 38. When the bracket 10 is debonded by urging the sections 12, 14 in directions toward each other, the elongated groove 38, in combination with the frangible web 37, facilitates concentration of stress in regions of the frangible web 37 that extend along a path adjacent to the longitudinal, central axis of the elongated groove 38 such that the bracket 10 tends to fracture along the narrowest section of the frangible web 37 while other portions of the bracket 10 remain intact. In this embodiment, the lingual-labial thickness of bridge section 15 increases when approaching the sections 12, 14 to reinforce the bridge section 15 and avoid undesirable stress concentrations in these areas.

Other lines of weakness are also possible. For example, the sections 12, 14 may be manufactured as initially separate components and the line of weakness may comprise a section of adhesive material that bonds the mesial and distal sections together. The line of weakness may also comprise an interference-fit coupling between the sections 12, 14 that bends or fractures during a debonding procedure. Further aspects and options relating to debonding ceramic brackets by urging mesial and distal sections of the brackets toward each other are described in U.S. Pat. No. 5,439,379 (Hansen et al.) and U.S. Pat. No. 5,366,372 (Hansen et al.).

As further exemplified in FIG. 3, the clip 39 is spaced away from the adjacent walls of the sections 12, 14 by gaps 60. During debonding, the gaps 60 allow sections 12, 14 to pivot to a sufficient degree, without interference, such that frangible web 37 will fracture and enable bracket 10 to separate from the patient's tooth. The gaps 60 may be located entirely either on the mesial or distal side of clip 39 or distributed between the mesial and distal sides of clip 39. The magnitude of the gaps 60 is determined by the margin by which the spacing between the sections 12, 14 exceeds the mesial-distal width of clip 39. Preferably, the spacing between the sections 12, 14 in a mesial-distal direction exceeds the mesial-distal width of clip 39 by at least about 50 microns, more preferably by at least about 65 microns, and most preferably by at least about 75 microns. Preferably, the spacing between the sections 12, 14 exceeds the mesial-distal width of clip 39 by at most about 200 microns, more preferably by at most about 175 microns, and most preferably by at most about 150 microns. In any case, however, excessive space on either side of the clip 39 is preferably avoided since it may produce a potential food or plaque trap. Excessive space may also unnecessarily increase the overall mesial-distal size of the bracket.

Various hand instruments may be used to urge sections 12, 14 toward each other to detach bracket 10 from a patient's tooth, including pliers such as those known in the profession as Weingart pliers, How pliers, or other orthodontic pliers such as described in U.S. Patent Publication No. 2006/0127835 (Soo et al.). Pliers for debonding ceramic brackets are generally well known to those of skill in the art.

Optionally and shown in the figures, the archwire slot 28 is defined on its occlusal, lingual and gingival sides by an archwire slot liner 29. In some embodiments, the archwire slot liner 29 does not have an occlusal wall 30 and/or gingival wall 34 extending along at least a portion of the archwire slot 28. Examples of liners are disclosed in U.S. Pat. Nos. 5,358,402 (Reed et al.), 5,380,196 (Kelly et al.), 5,439,379 (Hansen et al.) and 5,366,372 (Hansen et al.). The archwire slot liner 29 may be constructed, for example, from Type 316L stainless steel and have a thickness of about 0.05 mm. The archwire slot liner 29 is preferably bonded to the mesial and distal sections 12, 14 by a braze material such as an alloy comprising silver, copper, and at least 1.5% by weight titanium, based on the entire weight of the brazing alloy. Suitable brazing alloys are further described in published U.S. patent application No. 2008/0081309 entitled "ORTHODONTIC BRACKET WITH BRAZED ARCHWIRE SLOT LINER" (Wyllie II et al.) Other methods of attaching the archwire slot liner 29 to sections 12, 14 are also possible, including the use of an adhesive, a mechanical interlock, an interference fit or any combination of the foregoing. Use of archwire slot liner 29 is advantageous because it remains connected to both mesial section 12 and distal section 14 even after bridge section 15 is fractured in order to debond bracket 10. By holding sections 12, 14 together during and after debonding, archwire slot liner 29 conveniently allows removal of bracket 10 from the tooth in one piece.

Figure 6:
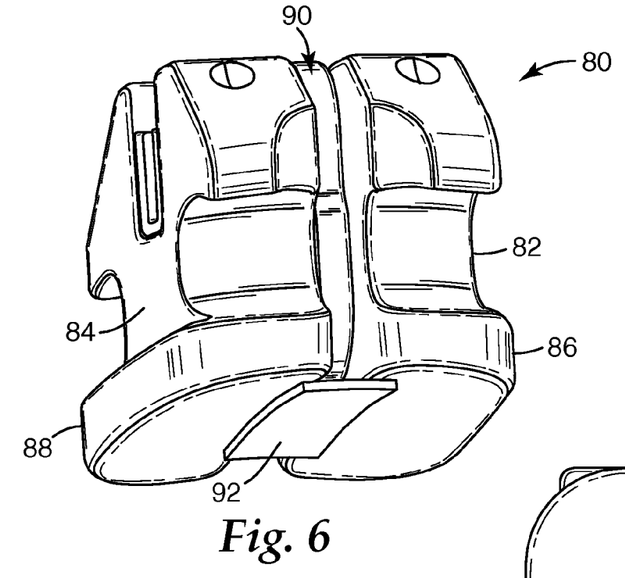
FIG. 6 is a perspective view looking at the gingival, lingual and distal sides of a bracket in accordance with another embodiment of the invention.
Figure 7:
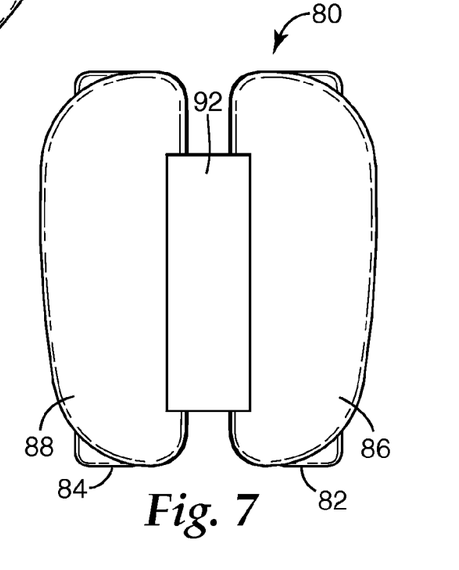
FIG. 7 is a bottom view looking at the lingual side of the bracket shown in FIG. 6.
Figure 8:
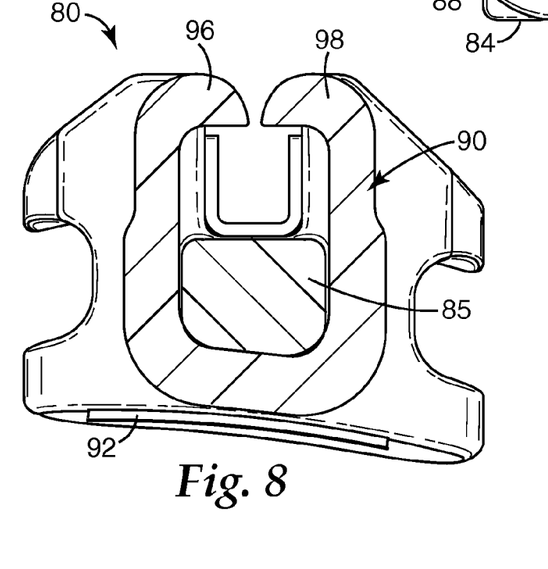
FIG. 8 is a side cross-sectional view of the bracket shown in FIGS. 6 and 7, showing in greater detail the shape of the latch.

Bracket 80, according to another embodiment of the invention, is shown in FIGS. 6-8 in perspective view, bottom view, and cross-sectional side view, respectively. As shown, the bracket 80 includes a mesial section 82 and distal section 84, connected to each other by a bridge section 85. The mesial section 82 and the distal section 84 include mesial base 86 and distal base 88, respectively, each preferably with a concave contour for bonding bracket 80 to the tooth.

A clip 90 has a generally "C"-shaped configuration including a pair of arm portions 96, 98. Bridge section 85 extends through clip 90. A stop member 92 is connected to the bases 86, 88 and contacts the lingual side of clip 90. By contacting the lingual side of clip 90, the stop member 92 prevents clip 90 from sliding in the lingual direction relative to bridge section 85 and possibly detaching from the bridge section 85. As shown, the stop member 92 extends over a portion of the gap between bases 86, 88 but may also extend over the entire gap from the occlusal edge to the gingival edge if so desired. Stop member 92 can be formed from a metal, ceramic, or polymeric material, and may comprise a solid sheet or porous material, such as a mesh or scrim. Together, mesial section 82, distal section 84, and stop member 92 constrain movement of clip 90 in both the mesial-distal and labial-lingual directions, thereby preventing clip 90 from inadvertently disengaging from bridge section 85 when bracket 80 is handled during a bonding procedure.

Although FIGS. 6, 7 show stop member 92 extending over only a small portion of bases 86, 88, it can optionally extend over a greater portion or even the entire surface of bases 86, 88. In this configuration, maximum contact area is achieved between stop member 92 and bases 86, 88 as well as between stop member 92 and the tooth surface. By extending over the entire surface of bases 86, 88, stop member 92 essentially becomes a "bonding pad" which engages the tooth surface during bonding. If stop member 92 is made flexible, as described in U.S. Pat. No. 6,786,720 (Kesling et al.), then its use as a bonding pad may impart some additional advantages such as facilitating debonding from the tooth surface.

Stop member 92 may be bonded to one or both of bases 86, 88 using an adhesive. Suitable adhesives include a wide variety of chemistries, such as ethylenically unsaturated compounds (with or without acid functionality), epoxy (oxirane) resins, vinyl ethers, photopolymerization systems, redox cure systems, glass ionomer cements, polyethers, polysiloxanes, and the like. More particularly, suitable photopolymerizable components that can be used as adhesives include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Useful ethylenically unsaturated compounds include acrylic acid esters, methacrylic acid esters, hydroxy-functional acrylic acid esters, hydroxy-functional methacrylic acid esters, and combinations thereof. Also suitable are polymerizable materials that contain both a cationically active functional group and a free radically active functional group in a single compound, including epoxy-functional acrylates, epoxy-functional methacrylates, and combinations thereof. If stop member 92 comprises a metal such as stainless steel, a braze such as described earlier may be used to bond stop member 92 to one or both of bases 86, 88.

Alternatives to using an adhesive or braze are also possible. For example, stop member 92 may be press fit or interference fit into the gap between mesial base 86 and distal base 88. In an interference fit, protrusions, hooks, undercuts or other retaining structures may be used to mechanically lock stop member 92 between bases 86, 88. Optionally, the lingual side of stop member 92 may be flush with the lingual side of bases 86, 88 by means of grooves cut or formed into bases 86, 88. If stop member 92 is not flush with bases 86, 88 it is preferably sufficiently thin so that it does not hinder mounting bracket 80 on the tooth surface. As another option, the lingual side of stop member 92 may be concave to matingly fit against the tooth surface and/or include retaining structure that facilitates bonding the bracket 80 directly to a patient's tooth. The retaining structure on stop member 92 can improve adhesion by forming a mechanical lock or chemical bond with a suitable adhesive disposed between the stop member 92 and the tooth surface. Retaining structure may include holes, grooves, particles, recesses, undercuts, a microetched surface, a chemical bond enhancement material, or any other structure, material or combination thereof. In the case where stop member 92 is a fibrous material such as a mesh or scrim, the fibers themselves can serve as the retaining structure.

If an adhesive is used to bond stop member 92 to bases 86, 88, the labial side of stop member 92 may similarly include retaining structure that facilitates adhesion between stop member 92 and bases 86, 88.

Similar to archwire slot liner 29, stop member 92 may provide an added advantage by holding together sections 12, 14 even after bracket 10 has been debonded from the tooth, thereby minimizing the number of bracket fragments after debonding. For this advantage to be realized, stop member 92 and bases 86, 88 should remain connected together and not delaminate or otherwise separate when bracket 10 is debonded from the tooth. As such, it is preferred that the overall strength of adhesion between stop member 92 and bases 86, 88 is greater than the overall strength of adhesion between stop member 92 and the underlying tooth. If retaining structure is used between the labial side of stop member 92 and the bases 86, 88, then this retaining structure may be configured to reduce the overall strength of adhesion between stop member 92 and bases 86, 88 relative to the overall strength of adhesion between stop member 92 and the underlying tooth. Preferably, the stop member 92 is sufficiently elastic so that it stretches and does not itself fracture as bases 16, 18 pivot away from each other during debonding of bracket 10. Finally it is preferred that the tensile modulus of stop member 92 is sufficiently low that it does not noticeably increase the force required to debond bracket 10 from the patient's tooth.

Another benefit in this configuration is shown in FIG. 8, which shows bracket 80 in cross-sectional view, looking in the mesial direction at clip 90. Compared to clip 39 in FIG. 2, clip 90 is simplified because clip protrusions are no longer needed to retain clip 90 on bridge section 85. The absence of protrusions, in turn, results in a clip structure that is more straightforward to manufacture. Moreover, the lack of protrusions helps facilitate assembly of bracket 80 because the arm portions 96, 98 do not need to be opened as wide when inserting clip 90 onto the bridge section 85 compared to inserting clip 39 onto bridge section 15 of bracket 10. As such, clip 90 is potentially subjected to less stress than clip 39, reducing the likelihood of damaging clip 90 during assembly. Aside from differences associated with clip 90 and stop member 92, other aspects of bracket 80 are similar to those of bracket 10 and need not be repeated here.

Brackets 10, 80 (including the sections 12, 14, 82, 84, the bridge sections 15, 85 and the tiewings (such as tiewings 23, 25) are preferably made from a translucent polycrystalline ceramic material exhibiting light transmittance sufficient for the brackets 10, 80 to assume the color of the underlying tooth. Preferably, the bridge sections 15, 85 integrally interconnect the sections 12, 14 and 82, 84 respectively such that the sections 12, 14 and 15 and the sections 82, 84 and 85 are manufactured as a unitary component. Examples of suitable ceramic materials are described in U.S. Pat. No. 6,648,638 (Castro et al.) and include aluminum oxide ceramic materials having an average grain size no larger than 1.0 micron. Other ceramic materials are also possible, including polycrystalline ceramic materials described in U.S. Pat. No. 4,954,080 (Kelly et al.) and single crystal ceramic materials described in U.S. Pat. No. 4,681,538 (DeLuca et al.). Other possible materials include porcelain, zirconia, glass, glass-ceramics and the like.

All patents and patent applications mentioned above are expressly incorporated by reference herein. Moreover, the embodiments described in detail above by way of illustration and examples are intended to exemplify the invention. However, it should be understood that various alternatives, modifications, and equivalents may be used and the above description should not be deemed to limit the scope of the invention as defined by the claims that follow.

The invention claimed is:

1. An orthodontic bracket comprising:
a mesial section;
a distal section;
a bridge section connecting the mesial section and the distal section, wherein the mesial section, the distal section and the bridge section comprise a ceramic material, and wherein the bridge section includes a line of weakness comprising a section having a reduced cross-sectional area and extending in a generally occlusal-gingival direction; and
wherein the bridge section further includes a groove that extends along the line of weakness and interrupts the continuity of the lingual surface of the bridge section;
an archwire slot extending across the mesial section and the distal section in a generally mesial-distal direction and located in a facial direction from the bridge section;
a recess that extends in a generally occlusal-gingival direction and is located in a lingual direction from the bridge section; and
a clip coupled to the bridge section for releasably retaining an archwire in the archwire slot, wherein at least a portion of the clip extends in the recess, wherein the clip has an opening facing the facial direction, wherein the bridge section extends through the clip, and wherein the clip surrounds the line of weakness, and wherein the line of weakness enables the bracket to be debonded from a tooth by pivoting one or both of the mesial and distal sections in directions toward each other.

2. The bracket of claim 1 further comprising an archwire slot liner that extends along the archwire slot.

3. The bracket of claim 2, wherein the archwire slot liner does not have an occlusal wall and/or gingival wall along at least a portion of the archwire slot.

4. The bracket of claim 1 wherein the clip releases the archwire from the archwire slot in a generally facial direction whenever the archwire exerts a force greater than about 1.4 kg on the bracket in the same direction.

5. The bracket of claim 1 wherein the clip releases the archwire from the archwire slot in a generally facial direction whenever the archwire exerts a force greater than about 0.7 kg on the bracket in the same direction.

6. The bracket of claim 5 wherein the clip comprises a shape-memory alloy.

7. The bracket of claim 5 wherein the bridge section includes a facial side, and wherein the clip includes protrusions that extend towards each other and contact the facial side of the bridge section.

8. The bracket of claim 7 wherein the clip further comprises a pair of tabs to facilitate assembly of the latch to the bridge section, wherein the tabs extend away from each other in generally occlusal and gingival directions.

9. The bracket of claim 8 wherein the pair of tabs is located in a facial direction from the pair of protrusions.

10. The bracket of claim 5 wherein the clip is generally "C"-shaped and comprises a pair of arm portions, wherein the arm members move away from each other to receive an archwire.

11. The bracket of claim 1 wherein the bracket includes at least one tiewing.

12. The bracket of claim 1, wherein the line of weakness comprises a frangible web.

* * * * *

UNITED STATES PATENT AND TRADEMARK OFFICE
CERTIFICATE OF CORRECTION

PATENT NO. : 7,686,613 B2 Page 1 of 1
APPLICATION NO. : 11/775253
DATED : March 30, 2010
INVENTOR(S) : Jirina V Pospisil It is certified that error appears in the above-identified patent and that said Letters Patent is hereby corrected as shown below:

Cover Page-Column 2 (abstract)
Line 7, Delete "patient' s" and insert -- patient's --, therefor.

Signed and Sealed this

Eighteenth Day of May, 2010

David J. Kappos
*Director of the United States Patent and Trademark Office*